United States Patent [19]

Sheets

[11] Patent Number: 4,813,953
[45] Date of Patent: Mar. 21, 1989

[54] INTRAOCULAR LENS

[76] Inventor: John H. Sheets, Rte. 5, Box 4801, Odessa, Tex. 79764

[21] Appl. No.: 21,317

[22] Filed: Mar. 3, 1987

[51] Int. Cl.[4] .............................................. A61F 2/16
[52] U.S. Cl. ........................................................ 623/6
[58] Field of Search ............................................ 623/6

[56] References Cited

U.S. PATENT DOCUMENTS

| | | | |
|---|---|---|---|
| 4,242,760 | 1/1981 | Rainin | 623/6 |
| 4,328,595 | 5/1982 | Sheets | 623/6 |
| 4,418,431 | 12/1983 | Feaster | 623/6 |
| 4,435,855 | 3/1984 | Pannu | 623/6 |
| 4,624,670 | 11/1986 | Bechert, II | 623/6 |
| 4,629,462 | 12/1986 | Feaster | 623/6 |
| 4,642,114 | 2/1987 | Rosa | 623/6 |

FOREIGN PATENT DOCUMENTS

| | | | |
|---|---|---|---|
| 0195881 | 10/1986 | European Pat. Off. | 623/6 |
| 2581535 | 11/1986 | France | 623/6 |
| WO85/02995 | 7/1985 | PCT Int'l Appl. | 623/6 |

OTHER PUBLICATIONS

Lens Styles from Cilco (Advertisement Brochure), Cilco, Inc., 1616 13th Ave., Huntington, West Virginia 25717, Oct. 1982, Posterior Chamber Lenses Style SM-1 and Style GR-1 Relied Upon.
Anterior Chamber and/or Posterior Chamber-Model 120, Feaster Dualens, (Advertisement page), Coburn Professional Products Div., P.O. Box 2498, Clearwater, FL 33517, 1 page, Aug. 1973.

Primary Examiner—Ronald L. Frinks
Attorney, Agent, or Firm—Mason, Fenwick & Lawrence

[57] ABSTRACT

An intraocular lens is unitarily formed with a lens body and two undulating shaped haptics formed of four segments which alternatingly curve in opposite directions to provide alternate troughs and protrusions which provide stability after positioning in the eye and which also cooperate with a unique implement to permit an easy positioning of the lens in the lens capsule following removal of the natural lens. Two disclosed embodiments of the lens comprise a vaulted lens and a non-vaulted lens.

18 Claims, 2 Drawing Sheets

U.S. Patent  Mar. 21, 1989  Sheet 1 of 2  4,813,953
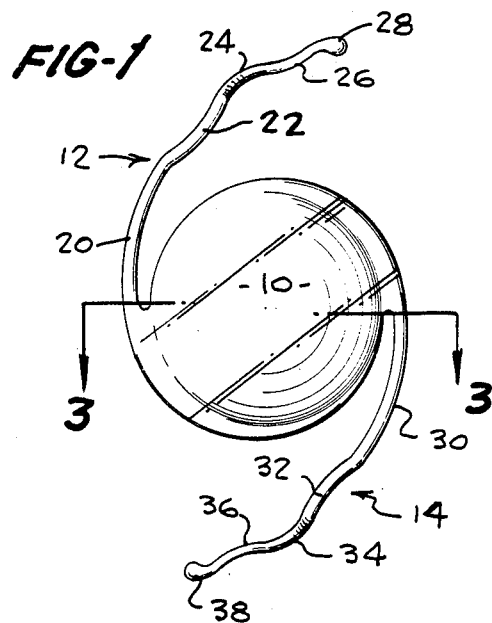
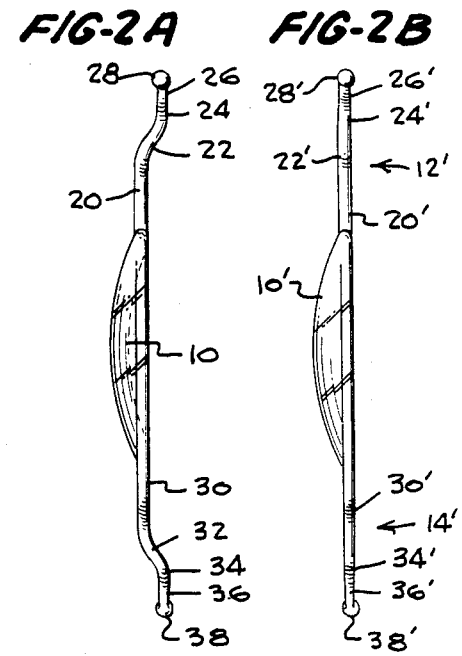
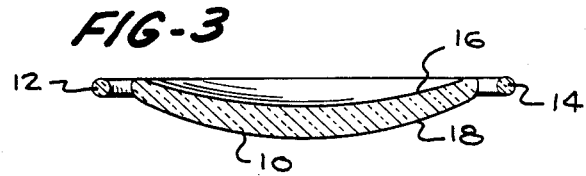
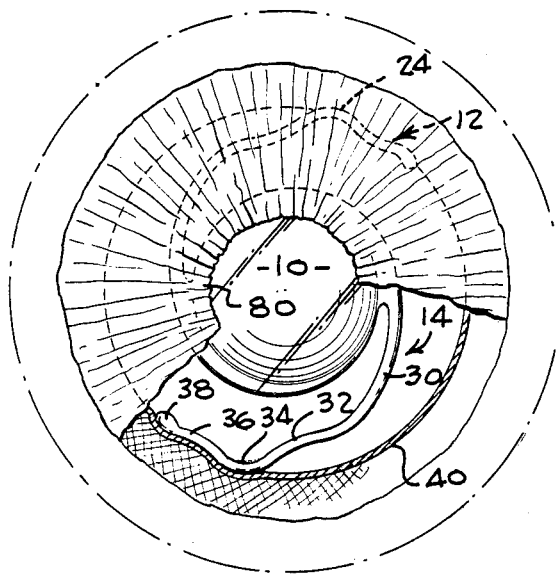
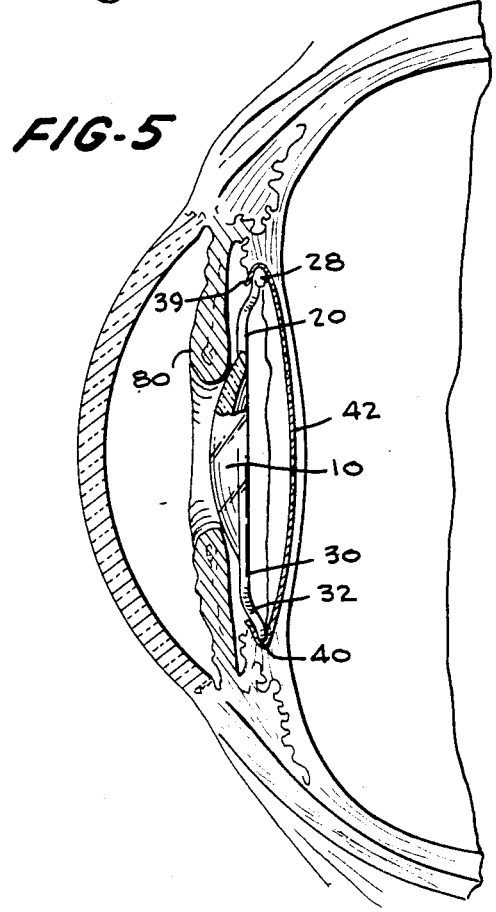

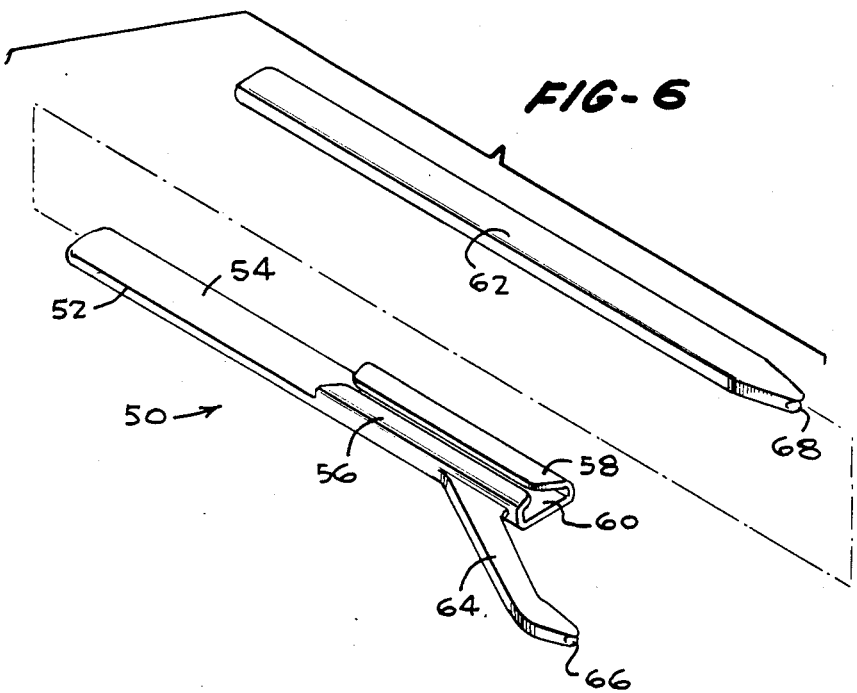
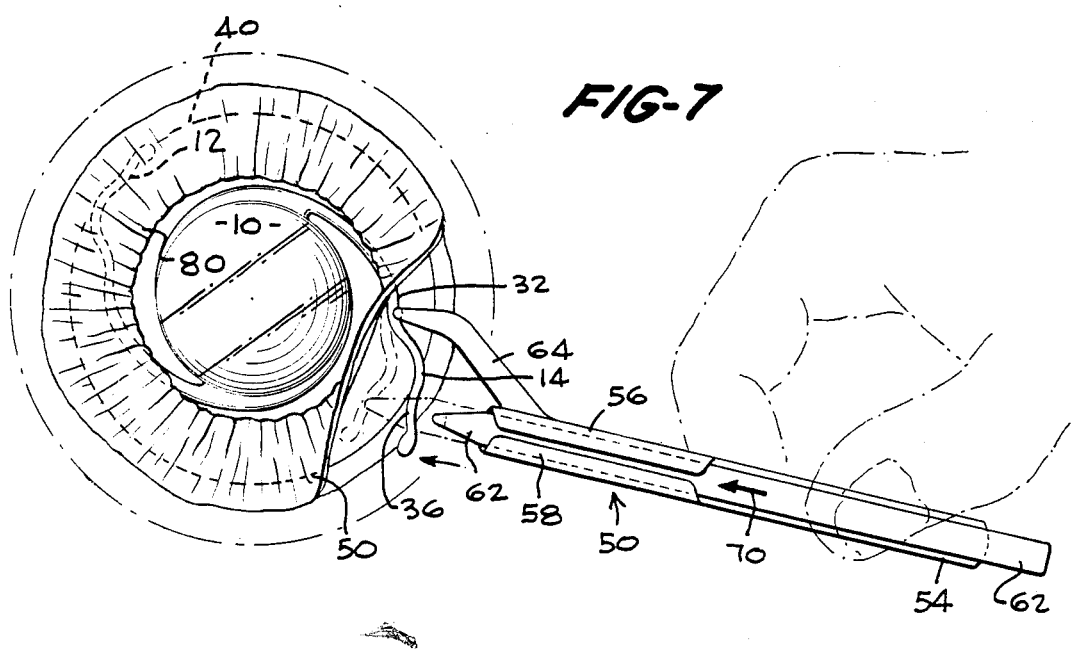

INTRAOCULAR LENS

BACKGROUND OF THE INVENTION

The present invention is in the field of intraocular lens devices for correction of aphakia by implantation in the posterior chamber of the human eye. With respect to prior art problems and proposed solutions thereto, reference is made to the description of the development of prior art intraocular lens and various prior patents and publications as discussed and cited in my earlier U.S. Pat. No. 4,328,595.

Notwithstanding the advances in the art represented by the above-noted and other prior art, problems of maintaining flexibility and stability of an intraocular lens in the eye have continued to occur. One particular problem resides in the fact that many of the prior known lenses that curve back upon themselves frequently malfunction as a consequence of the haptic moving out of position whenever the eye is compressed. Another problem resides in the fact that the implantation of an intraocular lens necessarily takes place in a restricted area to which access is difficult. Implantation has been effected by the use of conventional prior known surgical implements and by the use of newly developed special implements designed for implanting a particular type of lens. Unfortunately, many of the tools employed in lens implantation surgery are large in comparison to the size of the lens and are consequently cumbersome and difficult to use. Attempts to solve one or more of the aforementioned problems are demonstrated in U.S. Pat. Nos. 3,436,763; 3,673,616; 3,975,779; 4,080,709; 4,087,866; 4,092,743; 4,104,339; 4,122,556; 4,136,406; 4,198,714; 4,285,072; 4,370,760; 4,377,873; 4,414,359; 4,435,855; 4,451,938; 4,463,457; 4,463,458; 4,490,860; 4,476,591; 4,485,499; 4,490,860; 4,502,162; 4,502,163; 4,503,570; 4,504,981; 4,512,039; 4,512,040 and 4,513,546. Additionally, British Pat. No. 2,053,689 also illustrates an attempt to solve one or more of the aforementioned problems.

SUMMARY OF THE INVENTION

It is the primary object of the invention to provide a new and improved intraocular lens. A further object of the invention is a provision of a new and improved intraocular lens constructed in a manner so as to be easily inserted in the eye and so as to remain in a stable position after insertion.

Yet another object of the present invention is the provision of a new and improved intraocular lens manipulating implement for effecting the positioning of an intraocular lens in the eye.

Achievement of the aforementioned and other objects of the invention is enabled by the disclosed embodiments which comprise a vaulted intraocular lens and a non-vaulted intraocular lens. In both lenses the lens body is provided with a pair of haptics unitarily formed with the lens body and each comprising four end-to-end connected haptic segments which undulate in alternate manner from a single point inner connection of the innermost one of set segments to the lens body to an outer bulbous end tip on the outer end of the outermost one of the haptic segments. Stated differently, each haptic segment has a center of curvature with the center curvature of the adjacent haptic segments being on opposite sides of the haptic to provide the undulating shape to define a stepped outer surface at least partially engageable with the interior of the eye. The undulating shape of each haptic is of particular value in maintaining the haptic in firm position once it has been implemented. Moreover, the undulating shape is such as to permit usage of a special tool for effecting the implantation of the lens in the posterior chamber of the eye with a minimum of difficulty. In one lens embodiment, all of the haptic segments lie in a common plane so as to provide a non-vaulted construction. In the other lens embodiment the haptics include a canted haptic segment between the innermost segment adjacent the lens body and the third outward haptic segment so that the third and fourth haptic segments lie in a place spaced rearwardly of the plane of the lens body whereas the innermost haptic segment is in alignment with the lens body. There can be two identical undulating haptics. Each of said haptics includes four linear haptic segments joined in end-to-end array.

BRIEF DESCRIPTION OF THE DRAWINGS

FIG. 1 is a front elevation view of the preferred embodiment of the vaulted intraocular lens aspect of my invention;

FIG. 2A is a right side elevation view thereof;

FIG. 2B is a left side elevation view of a second embodiment;

FIG. 3 is a sectional view taken along lines 3—3 of FIG. 1;

FIG. 4 is a front elevation view illustrating the preferred embodiment after positioning in the eye with a portion of the eye being removed for clarity of illustration;

FIG. 5 is a sectional view through the eye illustrating the preferred embodiment following the implantation;

FIG. 6 is an exploded perspective view of a surgical implement aspect of the present invention; and FIG. 7 is a perspective view illustrating usage of the surgical implement of FIG. 6 during the positioning of an intraocular lens in the eye.

DESCRIPTION OF THE PREFERRED EMBODIMENTS

The preferred embodiment of the intraocular lens aspect of the invention comprises a convex-concave lens 10 formed of polymethylmethacrylate from which first and second haptic members 12 and 14 extend in a generally tangential manner. Lens 10 has a posterior surface 16 and an anterior face 18 as best shown in FIG. 3. It would also be possible to construct the lens 10 in other configurations such as convex-plano if desired.

The first undulating haptic 12 extends in the same rotative direction about the outer periphery of the lens body 10 and has an inner slightly curved portion 20 having a center curvature which is on the side of portion 20 facing lens 10. A second curve portion 22 is unitarily joined to the outer end of the inner portion 20 and has its center of curvature spaced outwardly from its side facing away from the lens 10. Similarly, a third curved portion 24 extends outwardly from the outer end of the second curved portion 22 in a unitary manner and has its center of curvature on its side facing lens 10. In like manner, a fourth curved portion 26 is unitarily joined and extends from the outer end of the third curved portion 24 and has its center of curvature spaced outwardly from its side facing away from the lens 10. Lastly, a bulbous end portion 28 is provided on the outer end of the fourth curved portion 26 and is positioned posteriorly of the anterior surface of the lens body. The bulbous distal portion 28 is spaced radially outwardly from the periphery of the lens body 10 in such a manner as to be directly engageable with an equatorial region of eye tissue within the interior of the eye so as to aid stable fixation of the intraocular lens within the eye. The second haptic 14 is identical to the first haptic 12 and similarly includes an inner curved portion 30 having its center of curvature facing its side facing the lens 10, a second curved portion 32 having a center of curvature outwardly of its side facing away from lens 10, a third curved portion 34 having a center of curvature facing its side facing the lens body 10 and an outer or fourth curved portion 36 having its center of curvature facing its surface which faces away from lens body 10. Additionally, the second haptic 14 includes an outer bulbous end portion 38.

It should further be observed that the second curved portion 22 is canted posteriorly from its inner end to its outer end as shown in FIG. 2A. Additionally, the fourth curved portion 26 is positioned in a plane perpendicular to the axis of the lens 10 and spaced approximately 0.3 mm posteriorly of the lens 10. The outer or fourth curved portion 26 and the bulbous end portion 28 are also positioned in the same plane as the third curved portion 24. For this vaulted embodiment, the bulbous distal portion 28 and the fourth portion or segment 26 are in a common plane and the first portion or segment 20 is in a plane parallel to the common plane and both of said planes are perpendicular to the optical axis of the lens body. In like manner, the second curved portion 32 of the second haptic is canted rearwardly in the same manner as portion 22 of the first haptic and third curved portion 34, fourth curved portion 36 and bulbous end portion 38 are positioned posteriorly of the lens body in the same plane as portions 24, 26 and 28 of the first haptic. Similarly, bulbous end portion 38 and fourth portion or segment 36 are in a common plane and the first portion or segment 30 is in a plane parallel to the common plane and both of said planes are perpendicular to the optical axis of the lens body.

In the non-vaulted embodiment of FIG. 2B, all portions of the first haptic 12 and the second haptic 14 lie in a common, plane perpendicular to the axis of lens 10 so as to provide a non-vaulted construction. More specifically, haptic 12' comprises inner portion 20', second curved portion 22', third curved portion 24', fourth curved portion 26' and bulbous end portion 28'. Similarly, the second haptic 14' comprises a first curved portion 30', a second curved portion 32', a third curved portion 34', a fourth curved portion 36' and a bulbous end portion 38'. It should be understood that the first and second haptics 12' and 14' are identical in appearance to the haptics 12 and 14 as viewed from the front as in FIG. 1; consequently, the location of the centers of curvature of portions 20', 22', 24' and 26' relative to the haptic are the same as those for portions 20, 22, 24 and 26 of first haptic 12.

Preparation of the eye for receiving either of the embodiments is effected by the conventional extracapsular cataract removal procedure in which the central portion of the anterior wall 39 of the lens capsule is removed so as to leave the equatorial region 40 and the posterior wall 42 of the lens capsule in position as shown in FIG. 5.

The manner in which the positioning of the disclosed embodiments of the invention in the eye is effected will now be discussed with initial reference being made to FIGS. 6 and 7. More specifically, a held held implement 50 is employed for accurately and easily manipulating the lens into permanent position in the eye. Implement 50 is formed of rigid metal or plastic and comprises a handle portion 52 having an upper surface 54 and first and second generally L-shaped guide plates 56 and 58 provided at one end for defining an opening 60 in which an elongated movable pusher 62 is positioned for axial reciprocation on surface 54. Pusher 62 and handle 52 are of rectangular transverse cross-section with pusher 62 being of less width than handle 52 as shown in FIG. 7. Additionally, a pusher finger 64 is fixedly connected to the side of handle portion 52 and includes a rearward portion which extends forwardly and laterally thereof as shown in FIG. 6 and a tapered distal portion oriented with its axis in a plane parallel to the axis of handle 52. The forward end of pusher finger 64 is provided with a U-shaped generally arcuate slot 66 dimensioned so as to be fittable over either of the haptics of the lens assembly. Similarly, the movable pusher 62 is provided with an identical transverse U-shaped or arcuate slot 68 on its forward end so as to be fittable over one of the haptics.

The manner in which the lens is positioned in the eye will now be discussed with reference being made to FIG. 7 in which the eye is illustrated with a previously effected incision used for removal of the natural lens by conventional procedures. The incision provided in the cornea 50 is of adequate size to permit the passage of the haptic 12 to pass through the incision and through the iris 80 so that it is positioned in the equatorial region 40 of the lens capsule as shown in FIG. 7. The positioning of the first haptic 12 is rather easily effected by the use of tweezers or similar surgical implements capable of manipulating the lens assembly. The hand held implement 50 is then used for positioning the second haptic 14 in the lens capsule with such positioning being generally accomplished in two steps. Firstly, implement 50 is grasped in the hand of a user with the movable pusher 62 being in a retracted position as shown in FIG. 7. The slot on the forward end of pusher finger 64 is engaged with the second curved portion 32 of haptic 14 and the implement is moved to the left to position the haptic in the dashed line position of FIG. 7. Movable pusher 62 is then moved forwardly in the direction of arrow 70 so that it engages the haptic in the fourth curved portion 36 and moves it forward to the position shown in dashed lines. Continued movement of the implement to the left permits the haptic 14 to pass through the iris into the posterior chamber of the eye so that it can then be released to move into the equatorial region 40 of the capsular bag. The U-shaped slots on the forward ends of pushers 62 and 64 permit the haptic to be manipulated forwardly and rearwardly since internal tension in the haptic maintains it in the U-shaped slots during the insertion procedure.

It will also be apparent that only a minimal amount of space is required for use of the implement 50 and that the movable pusher 62 can be easily adjusted to a desired position to give the exact amount of curvature necessary to pass the haptic 14 into the posterior chamber so as to position the lens assembly in the position shown in Fig. 5. Thus, the curved portions 32 and 36 of the haptic cooperate in a unique manner for permitting the positioning of the haptic in the posterior chamber. Also, the portions 34 and 38 in effect constitute foot portions engagable with the equatorial region 40 of the capsule to provide enhanced resistance to rotational movement of the lens. Consequently, the lens is extremely stable after positioning in the eye.

While preferred embodiments of the invention have been disclosed, it should be understood that those of skill in the art will undoubtedly conceive of equivalent variations which will not depart from the spirit and scope of the invention which is to be limited solely by the appended claims.

I claim:

1. An intraocular lens assembly comprising:
   a. a lens body having an anterior surface and a posterior surface relative to the eye of a user;
   b. at least two haptics, each of which extend outwardly from the outer periphery of said lens body at a single point of connection; and
   c. wherein at least one of said haptics comprises an undulating haptic extending in the same rotative direction about said outer periphery and including a plurality of curved haptic segments joined in end-to-end arrangement with adjacent haptic segments having their respective centers of curvature on opposite sides of said haptic to define a stepped outer surface at least partially engageable with the interior of the eye for holding the assembly therein, with one end of said one haptic being connected to said lens body, and another end of said haptic terminating in a bulbous distal portion spaced radially outwardly from said outer periphery in such a manner so as to be directly engageable with an equatorial region of eye tissue within the interior of the eye.

2. The lens assembly of claim 1 wherein said undulating haptic segments include:
   a. a first inner segment having an inner end and an outer end;
   b. a second segment having first and second ends;
   c. a third segment having inner and outer ends;
   d. a fourth segment having first and second ends; and
   e. said bulbous distal portion connected to the second end of said fourth segment.

3. A lens assembly as recited in claim 2 wherein said lens body and said undulating haptic are unitarily formed of plastic.

4. A lens assembly as recited in claim 3 wherein there are two identical undulating haptics.

5. A lens assembly as recited in claim 1 wherein there are two identical undulating haptics.

6. A lens assembly as recited in claim 5 wherein each of said undulating haptics includes four linear haptic segments joined in end-to-end array.

7. The lens assembly of claim 2 wherein said bulbous distal portion and said fourth segment are in a common plane and said plane is perpendicular to the optical axis of the lens body with the bulbous distal portion being positioned posteriorly of the anterior surface of the lens body.

8. A lens assembly as recited in claim 7 wherein said lens body and said undulating haptic are unitarily formed of plastic.

9. A lens assembly as recited in claim 8 wherein there are two identical undulating haptics.

10. A lens assembly as recited in claim 9 wherein each of said undulating haptics includes four linear haptic segments joined in end-to-end array.

11. A lens assembly of claim 1 wherein said one haptic consists essentially of an undulating haptic including a plurality of curved haptic segments joined in end-to-end arrangement to form a free end with adjacent haptic segments having their respective centers of curvature on opposite sides of said haptic to define a stepped outer surface at least partially engageable with the interior of the eye for holding the assembly therein, with one end of said one haptic being connected to said lens body, and another end of said haptic terminating in a bulbous distal portion.

12. A lens assembly of claim 7 wherein said third segment is in said common plane with said bulbous distal portion and said fourth segment.

13. A lens assembly of claim 12 wherein said third segment and said fourth segment are in said common plane spaced rearwardly of the plane of said lens body.

14. A lens assembly of claim 7 wherein said bulbous distal portion and said haptic segments are in a common plane.

15. A lens assembly of claim 1 capable of implantation in the posterior chamber of an eye.

16. A lens assembly of claim 12 wherein the said second segment is canted between said first inner segment and said third segment.

17. A lens assembly of claim 7 wherein said first segment is in a plane parallel to said common plane.

18. A lens assembly of claim 2 wherein said third segment and said bulbous distal portion comprise foot portions for engaging the interior of the eye and that resist rotational movement of said lens assembly.

* * * * *